(12) United States Patent
Glenn, Jr. et al.

(10) Patent No.: US 11,713,179 B2
(45) Date of Patent: Aug. 1, 2023

(54) REFILLABLE PRODUCT CONTAINING DISSOLVABLE SOLID ARTICLE

(71) Applicant: The Procter & Gamble Company, Cincinnati, OH (US)

(72) Inventors: Robert Wayne Glenn, Jr., Singapore (SG); Gloria Yu Hua Cheng, Singapore (SG); YunQin Lee, Singapore (SG); Todd Ryan Thompson, Loveland, OH (US); David Dean Tedesco, Liberty Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 69 days.

(21) Appl. No.: 17/320,444

(22) Filed: May 14, 2021

(65) Prior Publication Data

US 2021/0354903 A1 Nov. 18, 2021

Related U.S. Application Data

(60) Provisional application No. 63/025,191, filed on May 15, 2020.

(51) Int. Cl.
*B65D 65/46* (2006.01)
*B65D 81/32* (2006.01)
(Continued)

(52) U.S. Cl.
CPC ......... *B65D 81/3233* (2013.01); *A45D 40/24* (2013.01); *A61K 8/02* (2013.01);
(Continued)

(58) Field of Classification Search
CPC .... B65D 81/3233; B65D 65/46; B65D 83/00; B65D 85/804; B65D 75/00;
(Continued)

(56) References Cited

U.S. PATENT DOCUMENTS

D269,067 S 5/1983 Ballereau
5,566,732 A * 10/1996 Nelson ................. B67D 1/1236
141/351

(Continued)

FOREIGN PATENT DOCUMENTS

CN 105087173 A 11/2015
JP 2012511050 A 5/2012
(Continued)

OTHER PUBLICATIONS

U.S. Appl. No. 29/758,259, filed Nov. 13, 2020, YunQin Lee et al.
(Continued)

*Primary Examiner* — Frederick C Nicolas
(74) *Attorney, Agent, or Firm* — Alexandra S. Anoff

(57) ABSTRACT

Disclosed is a refillable product that includes a container containing two or more first dissolvable solid articles. The solid articles are characterized by a maximum dimension D and a minimum dimension z. The maximum dimension for D ranges from 1 mm to 300 mm and the minimum dimension for z ranges from 0.5 mm to 150 mm. The ratio between D and z ranges from 1:1 to 300:1. The refillable product also includes indicia for a user to put the dissolvable solid articles and a liquid carrier into another container. This product can provide an environment friendly product. For example, by not containing any liquid during transportation, the product can reduce energy consumption during the transportation.

14 Claims, 2 Drawing Sheets

(51) Int. Cl.
   *B65D 83/00* (2006.01)
   *A45D 40/24* (2006.01)
   *C11D 17/04* (2006.01)
   *B05B 7/00* (2006.01)
   *A61Q 19/00* (2006.01)
   *B65D 85/804* (2006.01)
   *A61K 8/02* (2006.01)
   *B65D 75/00* (2006.01)

(52) U.S. Cl.
   CPC ............... *A61Q 19/00* (2013.01); *B05B 7/00* (2013.01); *B65D 65/46* (2013.01); *B65D 83/00* (2013.01); *B65D 85/804* (2013.01); *C11D 17/044* (2013.01); *C11D 17/046* (2013.01); *A45D 2200/058* (2013.01); *A61K 2800/87* (2013.01); *B65D 75/00* (2013.01); *B65D 2203/00* (2013.01)

(58) Field of Classification Search
   CPC ............... B65D 2203/00; A45D 40/24; A45D 2200/058; C11D 17/044; C11D 17/046; A61K 2800/87; A61K 8/02; A61Q 19/00; B05B 7/00
   See application file for complete search history.

(56) References Cited

U.S. PATENT DOCUMENTS

| | | | |
|---|---|---|---|
| 7,325,688 | B1 | 2/2008 | Tessmer et al. |
| D594,752 | S | 6/2009 | Medema et al. |
| D613,177 | S | 4/2010 | Lee |
| D663,631 | S | 7/2012 | Mcdermott et al. |
| 8,268,764 | B2 | 9/2012 | Glenn, Jr. et al. |
| 8,349,786 | B2 | 1/2013 | Glenn, Jr. et al. |
| 8,415,287 | B2 | 4/2013 | Glenn, Jr. et al. |
| 8,461,090 | B2 | 6/2013 | Glenn, Jr. et al. |
| 8,461,091 | B2 | 6/2013 | Glenn, Jr. et al. |
| 8,466,099 | B2 | 6/2013 | Glenn, Jr. et al. |
| 8,476,211 | B2 | 7/2013 | Glenn, Jr. et al. |
| D695,132 | S | 12/2013 | Bouthillon |
| D705,663 | S | 5/2014 | Guichot |
| D709,652 | S | 7/2014 | Teller |
| D796,964 | S | 9/2017 | Staab |
| 9,855,203 | B2 | 1/2018 | Mcconaughy et al. |
| D816,506 | S | 5/2018 | Jones et al. |
| 10,017,316 | B2 * | 7/2018 | May .................. B65D 81/3222 |
| D852,052 | S | 6/2019 | Dalton |
| 10,315,838 | B1 * | 6/2019 | Bishara ............ B65D 75/5883 |
| D878,913 | S | 3/2020 | Castellanos et al. |
| D918,054 | S | 5/2021 | Papiernik |
| D922,880 | S | 6/2021 | Markoulis et al. |
| D928,624 | S | 8/2021 | Lim |
| D935,324 | S | 11/2021 | Bodum |
| D936,481 | S | 11/2021 | Newell |
| D936,483 | S | 11/2021 | Xie |
| D946,408 | S | 3/2022 | Mainguené |
| 2001/0022204 | A1 * | 9/2001 | Klima, Jr. ................ B67D 7/02 141/103 |
| 2003/0228336 | A1 * | 12/2003 | Gervasio .............. A61K 8/0212 206/530 |
| 2005/0284302 | A1 * | 12/2005 | Levin ................. B65D 51/2828 99/275 |
| 2008/0121655 | A1 | 5/2008 | Schultz et al. |
| 2010/0206764 | A1 | 8/2010 | Ketchum |
| 2011/0027328 | A1 | 2/2011 | Baig et al. |
| 2013/0303419 | A1 | 11/2013 | Glenn, Jr. et al. |
| 2014/0065076 | A1 * | 3/2014 | Hollander ............ A61K 49/101 424/9.454 |
| 2014/0065077 | A1 | 3/2014 | Hollander et al. |
| 2014/0105946 | A1 | 4/2014 | Glenn, Jr. et al. |
| 2015/0203275 | A1 * | 7/2015 | May .................. B65D 81/3222 206/219 |
| 2019/0282461 | A1 | 9/2019 | Glassmeyer et al. |
| 2020/0346838 | A1 | 11/2020 | Robinson et al. |
| 2020/0405587 | A1 | 12/2020 | Song |
| 2021/0354901 | A1 | 11/2021 | Glenn, Jr. et al. |
| 2021/0354902 | A1 | 11/2021 | Cheng et al. |

FOREIGN PATENT DOCUMENTS

| | | |
|---|---|---|
| JP | 2017008265 A | 1/2017 |
| JP | 2017519811 A | 7/2017 |
| JP | 2019177039 A | 10/2019 |
| JP | 1701938 S | 12/2021 |
| JP | 1704689 S | 1/2022 |
| WO | 2022056524 A1 | 3/2022 |

OTHER PUBLICATIONS

U.S. Appl. No. 29/758,260, filed Nov. 13, 2020, YunQin Lee et al.
U.S. Appl. No. 29/758,261, filed Nov. 13, 2020, YunQin Lee et al.
U.S. Appl. No. 29/783,322, filed May 12, 2021, YunQin Lee et al.
Database WPI Week 201617 Thomson Scientific, London, GB; AN 2015-81043C 71002806297, & CN 105 087 173 A (Zhoushan Sunlight Marine Technology Co) Nov. 25, 2015 (Nov. 25, 2015) abstract example 1.
Elegant Square Acrylic Cosmetic Refillable Cream Jar (30g). Online, published date unknown. Retrieved on Apr. 15, 2022, 1 pg. from URL: https://www.fasttech.com/product/9683542-elegant-square-acrylic-cosmetic-refillable-cream.
Foaming Shampoo Dispenser Bottle, Suream 4 Pack 8.45oz/250ml Blue Plastic Refillable Hand Pump Container for Lotion, Conditioner, Empty Small Square Bottle for Bathroom Body Wash, Kitchen Sink, Travel Online, published date unknown. Retrieved on Apr. 15, 2022, 1 pg. from URL: https://www.ubuy.co.id/en/product/D14CVKA-foamin.
All Office Actions; U.S. Appl. No. 17/320,404, filed May 14, 2021.
All Office Actions; U.S. Appl. No. 17/320,412, filed May 14, 2021.
All Office Actions; U.S. Appl. No. 17/580,180, filed Jan. 20, 2022.
All Office Actions; U.S. Appl. No. 29/758,259.
All Office Actions; U.S. Appl. No. 29/758,260.
All Office Actions; U.S. Appl. No. 29/758,261.
All Office Actions; U.S. Appl. No. 29/783,322, filed May 12, 2021.
U.S. Appl. No. 17/580,180, filed Jan. 20, 2022, to Ian-Ling Lim et al.

* cited by examiner

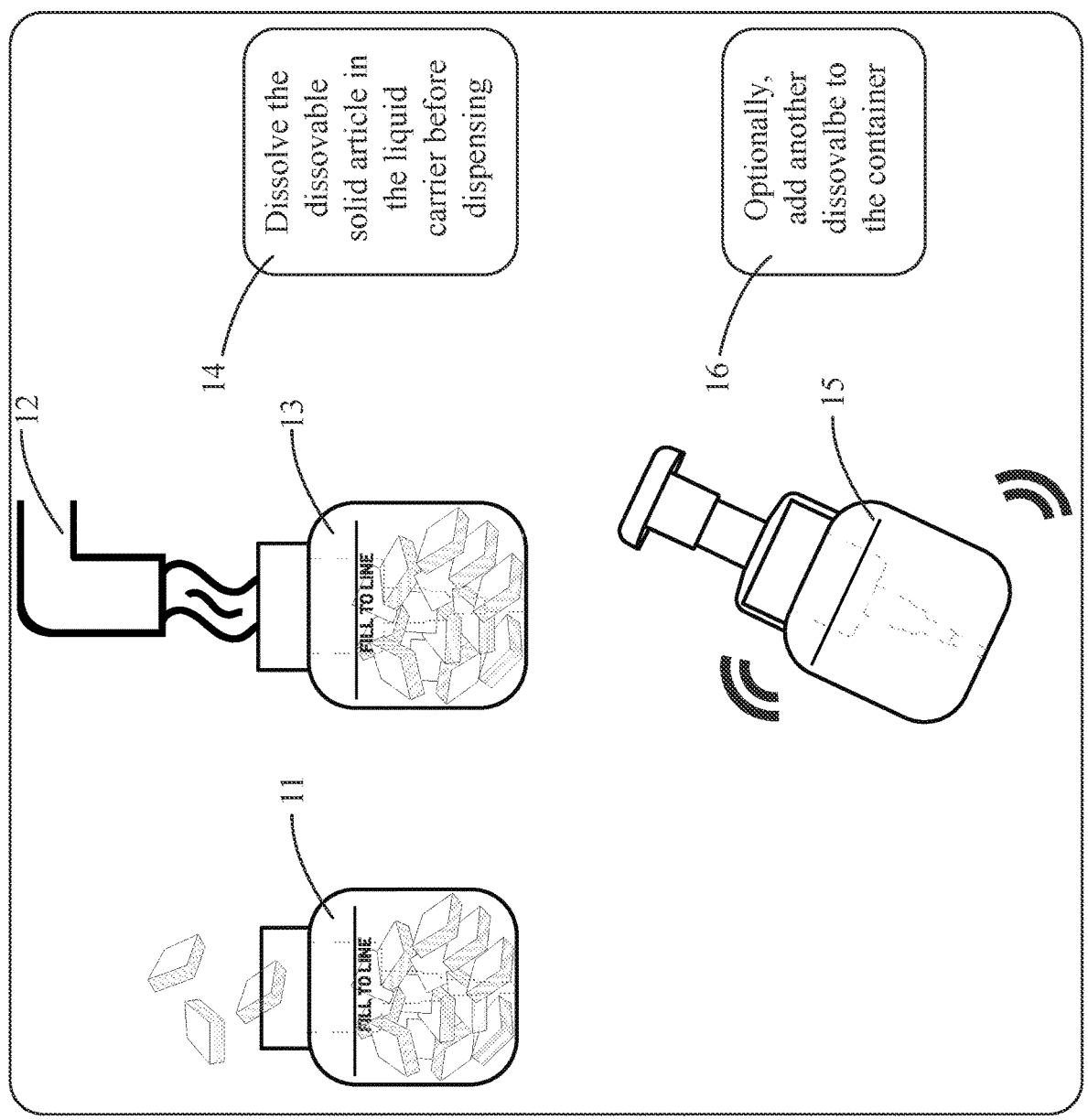

REFILLABLE PRODUCT CONTAINING DISSOLVABLE SOLID ARTICLE

FIELD OF THE INVENTION

The present invention relates to a refillable product containing dissolvable solid articles with a certain indicia. This provides environment friendly products. For example, by not containing any liquid during transportation, the products can reduce energy consumption for the transportation.

BACKGROUND OF THE INVENTION

Flexible and dissolvable solid articles comprising surfactant(s) and/or other active ingredients in a water-soluble polymeric carrier or matrix are well known. Such sheets are particularly useful for delivering surfactants and/or other active ingredients upon dissolution in water. In comparison with traditional granular or liquid forms in the same product category, such articles have better structural integrity, are more concentrated and easier to store, ship/transport, carry, and handle. In comparison with the solid tablet form in the same product category, such articles can provide faster dissolution and/or more aesthetic appeal to the consumers.

Such dissolvable solid articles are generally offered as a single dose product. For example, for personal care application, the dissolvable solid article is recommended to use by dissolving it on a hand and apply.

Therefore, there is a need for offering different product form and/or method of use of such dissolvable solid articles.

SUMMARY OF THE INVENTION

The present invention is directed to a refillable product comprising:
a container
two or more first dissolvable solid article contained in the container, which is characterized by a maximum dimension D and a minimum dimension z, wherein said maximum dimension D ranges from 1 mm to 300 mm, wherein said minimum dimension z ranges from 0.5 mm to 150 mm, and wherein the ratio between D and z ranges from 1:1 to 300:1; and
An indicia for a user to put the dissolvable solid articles and a liquid carrier into another container.

The refillable product of the above feature, wherein the refillable product comprises from 3 to 70 dissolvable solid articles, alternatively from 5 to 50, alternatively from 8 to 30, still alternatively from 11 to 20.

The refillable product of any of the preceding features, wherein the dissolvable solid article comprises two or more flexible, dissolvable, porous sheets.

The refillable product of any of the preceding features, wherein the dissolvable solid article is characterized by a density ranging from 0.050 g/cm cm$^3$ to about 0.380 g/cm cm$^3$, alternatively from 0.06 grams/cm cm$^3$ to 0.3 grams/cm cm$^3$, alternatively from 0.07 grams/cm cm$^3$ to 0.2 grams/cm cm$^3$, alternatively from 0.08 grams/cm cm$^3$ to 0.15 grams/cm3.

The refillable product of any of the preceding features, wherein the refillable product has an additional indicia to instruct the amount of the liquid carrier to add to the another container.

The refillable product of any of the preceding features, wherein the refillable product has an additional indicia for the user to add the dissolvable solid articles into the another container and then add the liquid carrier into the another container.

The refillable product of any of the preceding features, wherein the refillable product has an additional indicia for the user to dissolve the dissolvable solid article in the liquid carrier before dispensing from the another container.

The refillable product of any of the preceding features, wherein the refillable product has an additional indicia for the user to shake the another container after adding the dissolvable solid articles and the liquid carrier into the another container.

The refillable product of any of the preceding features, wherein the refillable product further comprises one or more second dissolvable solid articles, wherein the second dissolvable solid article is different from the first dissolvable solid article in its color, shape and/or size.

The refillable product of any of the preceding features, wherein the refillable product further comprises an indicia to add one or more second dissolvable solid articles into the another container, wherein the second dissolvable solid article is different from the first dissolvable solid article in its color, shape and/or size.

The refillable product of any of the preceding features, wherein the refillable product is free of any liquid contained together with the dissolvable solid articles.

The refillable product of any of the preceding features, wherein the liquid carrier is an aqueous carrier The refillable product of any of the preceding features, wherein the refillable product is a personal care product.

The present invention is also directed to a method of use of the refillable product of any of the preceding features, comprising:
a step to put the dissolvable solid articles from the container into the another container
a step to put the liquid carrier into the another container;
a step to dissolve the dissolvable solid articles in the liquid carrier;
a step to dispense a liquid mixture of the liquid carrier and the dissolvable solid articles dissolved in the liquid carrier, from the another container.

It provides at least one of the followings:
Environment friendly product. For example, by not containing any liquid during transportation, they can reduce energy consumption for the transportation.
Fast dissolution in the liquid carrier while providing aesthetic benefit especially when the dissolvable solid articles are colored and/or shaped.
In the refillable products, easy to refill compared to liquid products, in more detail, reduced messiness, reduced time to refill and/or reduced residue in the pouch.

These and other aspects of the present invention will become more apparent upon reading the following detailed description of the invention.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 2 shows the refillable product having indicia.

DETAILED DESCRIPTION OF THE INVENTION

Refillable Product

Figure 1A:
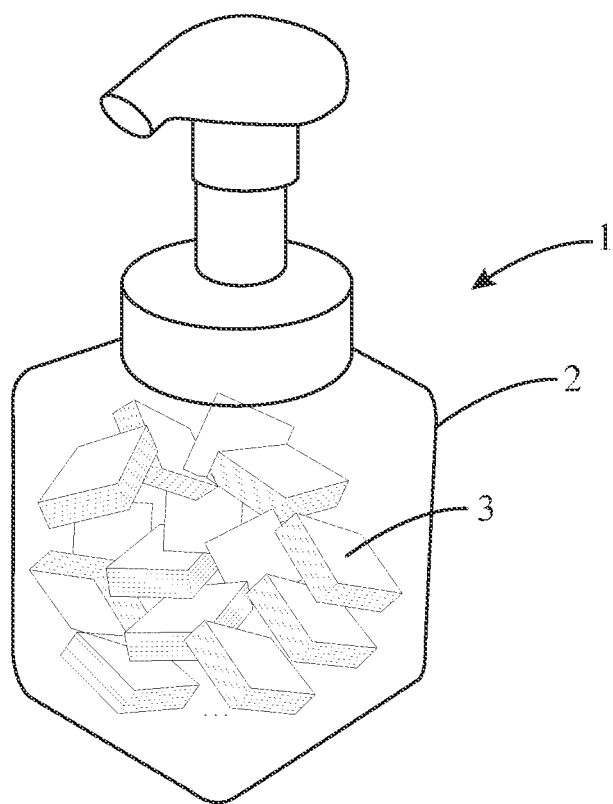
FIG. 1A is a perspective view of the refillable product.
Figure 1B:
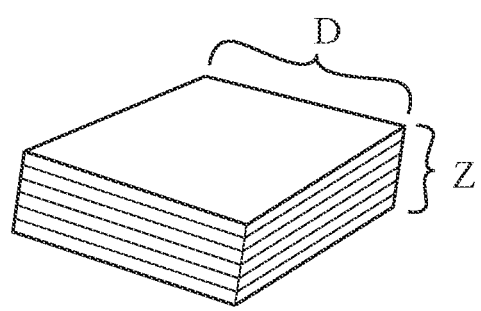
FIG. 1B shows an article.

FIG. 1A shows refillable product 1 comprising:
a container 2;
two or more first dissolvable solid articles 3 contained in the container 2, which is characterized by a maximum dimension D and a minimum dimension z, as shown in FIG. 1B, wherein said maximum dimension D ranges from 1 mm to 300 mm, wherein said minimum dimension z ranges from 0.5 mm to 150 mm, and wherein the ratio between D and z ranges from 1:1 to 300:1.

The refillable product is free of any liquid contained together with the dissolvable solid articles.

The refillable product can be any product including, for example, personal care products, home care products, surface cleaning products, general cleaning products. Alternatively, the product is a personal care product. Such personal products include, for example, personal cleansing products such as body, facial and/or hand cleansing products, skin care products such as Lotion, facial mist, gel, cream, hair care products such as shampoos and conditioners.

Indicia for Refillable Product

FIG. 2 shows the refillable product 10 has a first indicia 11 for a user to put the dissolvable solid articles into a container and a second indicia 12 for a user to put a liquid carrier into the another container 12.

Alternatively, the second indicia 12 can include refillable product 10 has an additional indicia 13 to instruct the amount of the liquid carrier to add to the another container.

In the example shown in FIG. 2, the refillable product 10 has both the first indicia 11 for the user to add the dissolvable solid articles into the another container and the second indicia 12 for a user to then add the liquid carrier into the another container 12.

Alternatively, the refillable product 10 has an additional third indicia 14 for the user to dissolve the dissolvable solid article in the liquid carrier before dispensing from the another container. alternatively, such additional The refillable product 10 can also include a fourth indicia 15 for the user to shake the container after adding the to help dissolve the dissolvable solid articles and into the liquid carrier in the another container.

The refillable product may further comprise a fifth indicia 16 to add one or more second dissolvable solid articles into the another container, wherein the second dissolvable solid article is different from the first dissolvable solid article in its color, shape and/or size.

Such indicia can be shown anywhere in the kit including, for example, on the container directly or indirectly via stickers and/or films, and on an additional document/sticker put together in the product. Such indicia can be anything including, for example, words, letters, numbers, shapes, colors, pictures, diagrams and any combinations thereof.

Method of Use the Refillable Product

Method of use of the refillable product comprises:
a step to put the dissolvable solid articles from the container into the another container
a step to put the liquid carrier into the another container;
a step to dissolve the dissolvable solid articles in the liquid carrier;
a step to dispense a liquid mixture of the liquid carrier and the dissolvable solid articles dissolved in the liquid carrier, from the another container.

Dissolving the articles can be done without doing anything proactively or by an appropriate way, for example, shaking the container.

Another Container Described for Refillable Product

The containers useful herein can be anything as long as it is capable of containing the dissolvable solid articles and also is capable of containing the liquid carrier. Representative containers useful herein include, for example, bottles with dispensers, both made by plastics, synthetic polymers, glasses and mixtures thereof. It is preferred that such containers useful herein are liquid-repellant, more specifically, aqueous carrier-repellant, and still more specifically water-repellant. The containers, especially bottles useful herein may be at least partially transparent or translucent, for increasing aesthetic benefit, for example, by showing the dissolvable solid articles contained inside. The container alternatively has a dispenser. The dispenser can be anything including, for example, a pump dispenser and a foam pump dispenser.

Container Used in Refillable Product

The container useful herein can be anything as long as it is capable of containing the dissolvable solid articles. Representative containers useful herein include, for example, flexible pouches made by plastics, synthetic polymers, natural polymers, and mixtures thereof. It may be preferred that such containers useful herein are water-repellant.

Dissolvable Solid Articles

Dissolvable solid articles useful herein are characterized by a maximum dimension D and a minimum dimension z, wherein said maximum dimension D ranges from 1 mm to 300 mm, wherein said minimum dimension z ranges from 0.5 mm to 150 mm, and wherein the ratio between D and z ranges from 1:1 to 300:1. The maximum dimension D herein means a longest length of the dissolvable articles, and the minimum dimension z herein means a shortest length of the dissolvable articles. For example, if the article has a spherical shape, the maximum dimension D is equal to the minimum dimension z.

The refillable product comprises from 2 to 70 dissolvable solid articles, alternatively from 5 to 50, alternatively from 8 to 30, still alternatively from 11 to 20, contained in the container.

The article can be in any shape, including, for example, sphere, cube, flower, heart, string, tassel, ribbon.

Alternatively, the maximum dimension D ranges from 3 mm to 150 mm, alternatively from 4 mm to 150 mm, still alternatively from 5 mm to 150 mm, and the minimum dimension z ranges from 3 mm to 50 mm, alternatively from 4 mm to 50 mm, still alternatively from 5 mm to 50 mm.

The dissolvable solid article can be in any color, and one article can have more than 2 different colors. For example, the dissolvable solid article can comprise a first part of a first color and a second part of a second color which is different from the first color, and wherein said first and second parts are visibly distinct from an external surface of said dissolvable solid article.

The dissolvable solid articles useful herein can be dissolved in the liquid carrier, for example, within 60 min, alternatively within 30 min, alternatively within 10 min without shaking the container or any other proactive mixings. With shaking the container or other proactive mixings, the dissolvable solid articles can be dissolved in the liquid carrier, for example, within 5 min, alternatively within 3 min, still alternatively within 2 min. The dissolvable solid articles useful herein can be dissolved in the liquid carrier, for example, by shaking the container from 1 to 50 times, alternatively from 1 to 30 times, still alternatively from 1 to 20 times, further alternatively from 1 to 10 times.

The term "solid" as used herein refers to the ability of an article to substantially retain its shape (i.e., without any visible change in its shape) at 20° C. and under the atmospheric pressure, when no external force is applied thereto.

The term "flexible" as used herein refers to the ability of an article to withstand stress without breakage or significant fracture when it is bent at 90° along a center line perpendicular to its longitudinal direction. Alternatively, such article can undergo significant elastic deformation and is characterized by a Young's Modulus of no more than 5 GPa, alternatively no more than 1 GPa, alternatively no more than 0.5 GPa, alternatively no more than 0.2 GPa.

The dissolvable solid article useful herein is capable of dissolving in the liquid, especially aqueous carrier to form an aqueous composition.

The dissolvable solid article can comprise components selected from the group consisting of surfactants, water-soluble polymer structurants, plasticizers, rheology modifiers, other optional ingredients, and mixtures thereof.

The dissolvable solid article is alternatively porous, and can be characterized by a density ranging from 0.050 g/cm$^3$ to about 0.380 g/cm$^3$, alternatively from 0.06 grams/cm$^3$ to 0.3 grams/cm$^3$, alternatively from 0.07 grams/cm$^3$ to 0.2 grams/cm$^3$, alternatively from 0.08 grams/cm$^3$ to 0.15 grams/cm$^3$. The dissolvable solid structure of the present invention can be provided in the form of a dissolvable solid article comprising one or more flexible, dissolvable, porous sheets, wherein each of said two or more sheets is characterized by being an open-celled foam, a fibrous structure, and the like. The porous sheets can be optionally bonded together via a bonding means (e.g., heat, moisture, ultrasonic, pressure, and the like).

The term "open celled foam" or "open cell pore structure" as used herein refers to a solid, interconnected, polymer-containing matrix that defines a network of spaces or cells that contain a gas, typically a gas (such as air), while maintaining the physical strength and cohesiveness of the solid. The interconnectivity of the structure may be described by a Percent Open Cell Content, which is measured by Test 1 disclosed hereinafter. The dissolvable solid article useful herein can be characterized by a Percent Open Cell Content of from 80% to 100%.

Test 1: Percent Open Cell Content of the Sheet Article

The Percent Open Cell Content is measured via gas pycnometry. Gas pycnometry is a common analytical technique that uses a gas displacement method to measure volume accurately. Inert gases, such as helium or nitrogen, are used as the displacement medium. A sample of the solid sheet article of the present invention is sealed in the instrument compartment of known volume, the appropriate inert gas is admitted, and then expanded into another precision internal volume. The pressure before and after expansion is measured and used to compute the sample article volume.

ASTM Standard Test Method D2856 provides a procedure for determining the percentage of open cells using an older model of an air comparison pycnometer. This device is no longer manufactured. However, one can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the open cell volume as measured by the Accupyc, according to the following equation:

$$\text{Open cell percentage} = \text{Open cell volume of sample} / \text{Geometric volume of sample} * 100$$

It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in "Analytical Methods in Fine particle Technology" by Clyde Orr and Paul Webb.

The dissolvable solid articles can be characterized by Overall Average Pore Size of from 100 µm to 2000 µm, as measured by the Micro-CT method described in Test 2 hereinafter. The Overall Average Pore Size defines the porosity of the dissolvable solid article.

The dissolvable solid articles can be characterized by an Average Cell Wall Thickness or Average Filament Diameter of from 1 µm to 200 µm, alternatively from 10 µm to 100 µm, alternatively from 20 µm to 80 µm; still alternatively from about 25 µm to 60 µm, as measured by Test 2 hereinafter.

Test 2: Micro-Computed Tomographic (µCT) Method for Determining Overall or Regional Average Pore Size and Average Cell Wall Thickness of the Open Cell Foams (OCF)

Porosity is the ratio between void-space to the total space occupied by the OCF. Porosity can be calculated from µCT scans by segmenting the void space via thresholding and determining the ratio of void voxels to total voxels. Similarly, solid volume fraction (SVF) is the ratio between solid-space to the total space, and SVF can be calculated as the ratio of occupied voxels to total voxels. Both Porosity and SVF are average scalar-values that do not provide structural information, such as, pore size distribution in the height-direction of the OCF, or the average cell wall thickness of OCF struts.

To characterize the 3D structure of the OCFs, samples are imaged using a µCT X-ray scanning instrument capable of acquiring a dataset at high isotropic spatial resolution. One example of suitable instrumentation is the SCANCO system model 50 µCT scanner (Scanco Medical AG, Brtittisellen, Switzerland) operated with the following settings: energy level of 45 kVp at 133 µA; 3000 projections; 15 mm field of view; 750 ms integration time; an averaging of 5; and a voxel size of 3 µm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned OCF samples are normally prepared by punching a core of approximately 14 mm in diameter. The OCF punch is laid flat on a low-attenuating foam and then mounted in a 15 mm diameter plastic cylindrical tube for scanning. Scans of the samples are acquired such that the entire volume of all the mounted cut sample is included in the dataset. From this larger dataset, a smaller sub-volume of the sample dataset is extracted from the total cross section of the scanned OCF, creating a 3D slab of data, where pores can be qualitatively assessed without edge/boundary effects.

To characterize pore-size distribution in the height-direction, and the strut-size, Local Thickness Map algorithm, or LTM, is implemented on the subvolume dataset. The LTM Method starts with a Euclidean Distance Mapping (EDM) which assigns grey level values equal to the distance each void voxel is from its nearest boundary. Based on the EDM data, the 3D void space representing pores (or the 3D solid space representing struts) is tessellated with spheres sized to match the EDM values. Voxels enclosed by the spheres are assigned the radius value of the largest sphere. In other words, each void voxel (or solid voxel for struts) is assigned the radial value of the largest sphere that that both fits within the void space boundary (or solid space boundary for struts) and includes the assigned voxel.

The 3D labelled sphere distribution output from the LTM data scan can be treated as a stack of two dimensional images in the height-direction (or Z-direction) and used to estimate the change in sphere diameter from slice to slice as a function of OCF depth. The strut thickness is treated as a 3D dataset and an average value can be assessed for the whole or parts of the subvolume. The calculations and measurements were done using AVIZO Lite (9.2.0) from Thermo Fisher Scientific and MATLAB (R2017a) from Mathworks.

The dissolvable solid articles can be characterized by a Specific Surface Area of from 0.03 m2/g to 0.25 m2/g, alternatively from 0.04 m2/g to 0.22 m2/g, alternatively from 0.05 m2/g to 0.2 m2/g, alternatively from 0.1 m2/g to 0.18 m2/g. as measured by Test 3 described hereinafter. The Specific Surface Area of the solid sheet of the present invention may be indicative of its porosity and may impact its dissolution rate, e.g., the greater the Specific Surface Area, the more porous the sheet and the faster its dissolution rate.

Test 3: Specific Surface Area of the Sheet Article

The Specific Surface Area of the flexible, porous, dissolvable solid sheet article is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

The dissolvable solid articles can be characterized by a final moisture content of from 0.5% to 25%, alternatively from 1% to 20%, alternatively from 3% to 10%, by weight of said article as measured by Test 4 hereinafter. An appropriate final moisture content in the resulting solid sheet may ensure the desired flexibility/deformability of the sheet, as well as providing soft/smooth sensory feel to the consumers. If the final moisture content is too low, the sheet may be too brittle or rigid. If the final moisture content is too high, the sheet may be too sticky, and its overall structural integrity may be compromised.

Test 4: Final Moisture Content of the Sheet Article

Final moisture content of the solid sheet article of the present invention is obtained by using a Mettler Toledo HX204 Moisture Analyzer (S/N B706673091). A minimum of 1 g of the dried sheet article is placed on the measuring tray. The standard program is then executed, with additional program settings of 10 minutes analysis time and a temperature of 110° C.

First and Second Dissolvable Solid Articles

Two or more different dissolvable solid articles can be used. For example, a first dissolvable solid articles and a second dissolvable solid articles can be used together, wherein the first and second dissolvable solid articles are different in perfumes, compositions, and/or different benefits. Alternatively, the second dissolvable solid is different from the first dissolvable solid article in its color, shape and/or size.

Liquid Carrier

Liquid carrier useful herein can be anything and selected according to the compatibility with other components, and other desired characteristics of the product. The liquid carrier is an aqueous carrier, and alternatively water especially in personal care.

EXAMPLES

Refillable Product
(1-1) Details of Container
Flexible pouch
(1-2) Details of Another Container:
Bottle with foam dispenser, both made by plastics, bottle is fully transparent. internal capacity (volume) of the bottle: 250 ml
(2) Details of First Dissolvable Solid Articles
Maximum dimension D: 1.7 cm
Minimum dimension z: 0.7 cm
Number of the First dissolvable solid articles contained in the container: Approximately 40 pieces
Sum of the volume of the first dissolvable articles: 100 cm$^3$
Density: about 0.1 g/cm$^3$
Color: 6 layered sheets using 5 colors (white, pink, blue, yellow, purple),
Shape: Cube (1.7 cm×1.7 cm×0.7 cm) comprising layered 6 sheets
Application: Personal cleansing
The product is free of any liquid contained together with the first dissolvable solid articles
(3) Details of Indicia
Adding the first dissolvable articles into the container, and then adding water is printed on the flexible pouch by pictures.
The amount of water is printed in words (e.g. add 200 ml of water) on the flexible pouch. Shaking the container after adding the dissolvable solid articles and the liquid carrier into the container, is printed on the flexible pouch by pictures.

(4) Details of Method

The above refillable product is used by the following method comprising:

First step to put the dissolvable solid articles into the another container

Second step to put the liquid carrier into the another container;

Third step to dissolve the dissolvable solid articles in the liquid carrier by shaking the another container;

Fourth step to dispense a liquid mixture of the liquid carrier and the dissolvable solid articles dissolved in the liquid carrier, from the another container.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A refillable product comprising:
  a container;
  from about 8 to about 30 first dissolvable solid article contained in the container, which is characterized by a maximum dimension D and a minimum dimension z, wherein said maximum dimension D ranges from 5 mm to 150 mm, wherein said minimum dimension z ranges from 5 mm to 50 mm, and wherein the dissolvable solid articles are porous and comprise a density from about 0.050 g/cm$^3$ to about 0.380 g/cm$^3$; and
  an indicia for a user to put the dissolvable solid articles and a liquid carrier into another container; wherein the refillable product further comprises an indicia to instruct the amount of the liquid carrier to add to the another container; and wherein the dissolvable solid articles are dissolvable in the liquid carrier within 2 min.

2. The refillable product of claim 1, wherein the refillable product comprises from about 11 to about 20 dissolvable solid articles.

3. The refillable product of claim 1, wherein the dissolvable solid article consists of two or more flexible, dissolvable, porous sheets.

4. The refillable product of any of claim 1, wherein the dissolvable solid article comprises a density ranging from about 0.06 grams/cm$^3$ to about 0.3 grams/cm$^3$.

5. The refillable product of any of claim 4, wherein the dissolvable solid article comprises a density ranging from about 0.07 grams/cm$^3$ to about 0.2 grams/cm$^3$.

6. The refillable product of any of claim 5, wherein the dissolvable solid article comprises a density ranging from about 0.08 grams/cm$^3$ to about 0.15 grams/cm$^3$.

7. The refillable product of any of claim 1, wherein the refillable product has an additional indicia for the user to add the dissolvable solid articles into the another container and then add the liquid carrier into the another container.

8. The refillable product of any of claim 7, wherein the refillable product has an additional indicia for the user to dissolve the dissolvable solid article in the liquid carrier before dispensing from the another container.

9. The refillable product of any of claim 8, wherein the refillable product has an additional indicia for the user to shake the another container after adding the dissolvable solid articles and the liquid carrier into the another container.

10. The refillable product of claim 1, wherein the refillable product further comprises an indicia to add one or more second dissolvable solid articles into the another container.

11. The refillable product of claim 10, wherein the refillable product further comprises one or more second dissolvable solid articles, wherein the second dissolvable solid article comprises a different color, shape and/or size as compared to the first solid article.

12. The refillable product of claim 1, wherein the refillable product is free of any liquid contained together with the dissolvable solid articles.

13. The refillable product of claim 1, wherein the liquid carrier is an aqueous carrier.

14. The refillable product of claim 1, wherein the refillable product is a personal care product.

* * * * *